United States Patent [19]

Martin

[11] 3,997,603
[45] Dec. 14, 1976

[54] HERBICIDAL HALO-DI-ALKYL BENZENESULFONAMIDES

[75] Inventor: Elmore Louis Martin, Wilmington, Del.

[73] Assignee: E. I. Du Pont de Nemours and Company, Wilmington, Del.

[22] Filed: Oct. 15, 1974

[21] Appl. No.: 515,071

Related U.S. Application Data

[60] Division of Ser. No. 334,411, Feb. 21, 1973, Pat. No. 3,888,897, which is a continuation-in-part of Ser. No. 243,404, April 12, 1972, abandoned.

[52] U.S. Cl. .................. 260/556 AR; 71/103; 260/465 E; 260/556 B
[51] Int. Cl.² .................. C07C 143/78; A01N 9/16
[58] Field of Search .............. 260/556 B, 556 AR; 71/103

[56] References Cited

UNITED STATES PATENTS

| | | | |
|---|---|---|---|
| 3,246,974 | 4/1966 | Brokke et al. | 71/103 X R |
| 3,501,526 | 3/1970 | Wei et al. | 260/556 B |
| 3,518,075 | 6/1970 | Brokke et al. | 71/103 |
| 3,642,892 | 2/1972 | Baker | 260/556 AR |
| 3,799,760 | 3/1974 | Stephens | 71/103 |

FOREIGN PATENTS OR APPLICATIONS

| | | | |
|---|---|---|---|
| 17,789 | 8/1965 | Japan | 260/556 AR |

*Primary Examiner*—Allen B. Curtis
*Assistant Examiner*—Thomas A. Waltz

[57] ABSTRACT

Certain substituted cyanobenzenesulfonamides, nitrobenzenesulfonamides, trifluoromethylbenzenesulfonamides, halobenzenesulfonamides, and cyanomethylbenzenesulfonamides are effective preemergence and postemergence herbicides, which may be used for selective weed control in certain crops.

2 Claims, No Drawings

HERBICIDAL HALO-DI-ALKYL BENZENESULFONAMIDES

This is a division of my copending application, Ser. No. 334,411, filed Feb. 21, 1973, now U.S. Pat. 3,888,897 which is a continuation-in-part of our application, Ser. No. 243,404, filed Apr. 12, 1972, now abandoned.

BACKGROUND OF THE INVENTION

This invention relates to a class of substituted cyanobenzenesulfonamides, halobenzenesulfonamides, nitrobenzenesulfonamides, trifluoromethylbenzenesulfonamides, and cyanomethylbenzenesulfonamides, to the use of these classes of compounds as herbicides, and to herbicidal compositions containing them as active ingredients.

Although a large number of herbicides are presently on the market, there is a continual need for more active, more selective, and reasonably priced herbicides that could be used in the presence of commercial crops.

SUMMARY OF THE INVENTION

Certain cyanobenzenesulfonamides, halobenzenesulfonamides, nitrobenzenesulfonamides, trifluoromethylbenzene-sulfonamides, and cyanomethylbenzenesulfonamides exhibit selective herbicidal activity and can be used in the presence of valuable crops, e.g., soybeans, wheat, corn, rice, peanuts, and cotton. These compounds are represented by Formula (1).

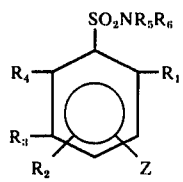

Wherein
Z is cyano, halogen, cyanomethyl, nitro or trifluoromethyl;
$R_1$, $R_2$, $R_3$ and $R_4$ are the same or different and are independently selected from the group consisting of hydrogen, alkyl of 2 to 7 carbon atoms and halogen provided that:
 a. two of $R_1$, $R_2$, $R_3$ and $R_4$ are alkyl of 2 to 7 carbon atoms;
 b. no alkyl groups are ortho to each other;
 c. a least one of $R_1$, $R_2$, $R_3$ and $R_4$ is alkyl of 3 to 7 carbon atoms;
 d. two of $R_1$, $R_2$, $R_3$ and $R_4$ are independently hydrogen or halogen;
 e. the total carbon content of $R_1$, $R_2$, $R_3$ and $R_4$ is not greater than 9 carbon atoms; and
 f. each alkyl group has from 2 to 3 carbon atoms in a straight chain from the point of attachment to the aromatic ring; and
 g. when Z is nitro, both $R_1$ and $R_3$ must be alkyl groups.
$R_5$ is hydrogen, alkyl of 1 to 3 carbon atoms, allyl or propynyl;
$R_6$ is hydrogen, alkyl of 1 to 3 carbon atoms, allyl, propynyl, lithium, sodium, potassium, calcium or acyl of 1 to 3 carbon atoms; and $R_5$ and $R_6$ together can form

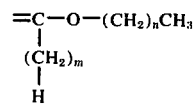

Where m is 0 or 1 and n is 0 or 1.

Preferred because of higher herbicidal activity are those compounds of Formula (1) where each of $R_2$, $R_4$ and $R_5$ is hydrogen; $R_6$ is hydrogen, lithium, sodium or potassium; $R_1$ and $R_3$ are each independently alkyl of 3 to 5 carbon atoms; and Z is cyano, bromine or chlorine.

Most preferred because of its safety to cotton and peanuts is 4-cyano-2,5-diisopropylbenzenesulfonamide and because of its safety to rice is 4-chloro-2,5-diisopropylbenzenesulfonamide.

The halobenzenesulfonamide compounds are intermediates in the synthesis of the above cyanobenzenesulfonamides which in turn can be used to prepare the cyanomethylbenzenesulfonamides and trifluoromethylbenzenesulfonamides in those cases where shorter routes are not applicable.

DETAILED DESCRIPTION OF THE INVENTION

Compounds of Formula (1) can be prepared by many processes based on methods generally well-known in the art. The starting materials for these compounds are alkylbenzenes. Many of these are commercially available. Those not available are easily synthesized by well-known methods. Simple cyanobenzenesulfonamides can be made, for instance, by bromination of the corresponding dialkylbenzenes, chlorosulfonation of the resulting bromodialkylbenzenes, amidation of the resulting bromodialkylbenzenesulfonyl chlorides with ammonia or an alkyl- or dialkylamine, and replacement of the bromo group with a cyano group. This reaction is illustrated by the following equations. The illustration shows reactions beginning with 1,4-diisopropylbenzene. Other appropriately substituted alkylbenzenes can be substituted for this compound.

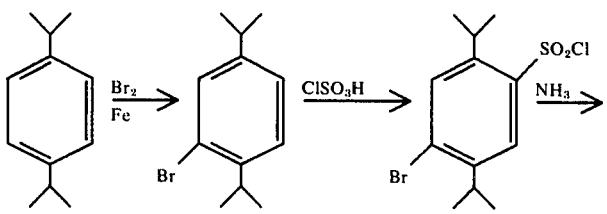

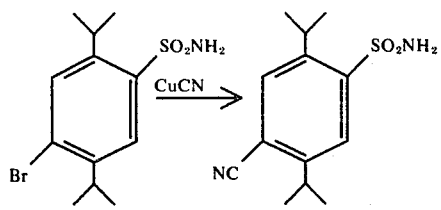

Halogenated cyanobenzenesulfonamides can be prepared in a similar manner as shown below.

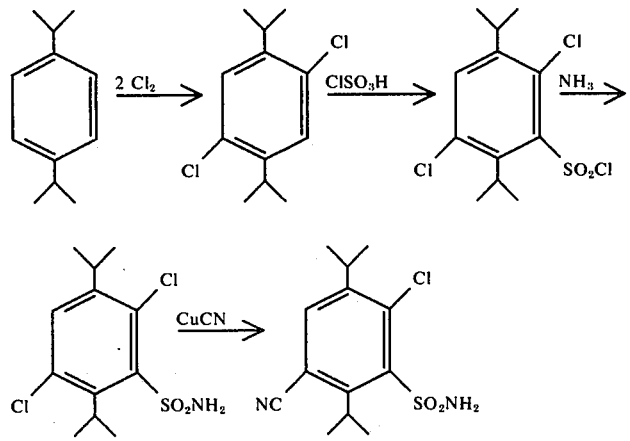

Cyanomethylbenzenesulfonamides can be prepared from cyanobenzenesulfonamides by well-known methods for the conversion of a cyano group to a cyanomethyl group. This conversion is illustrated by the following equations:

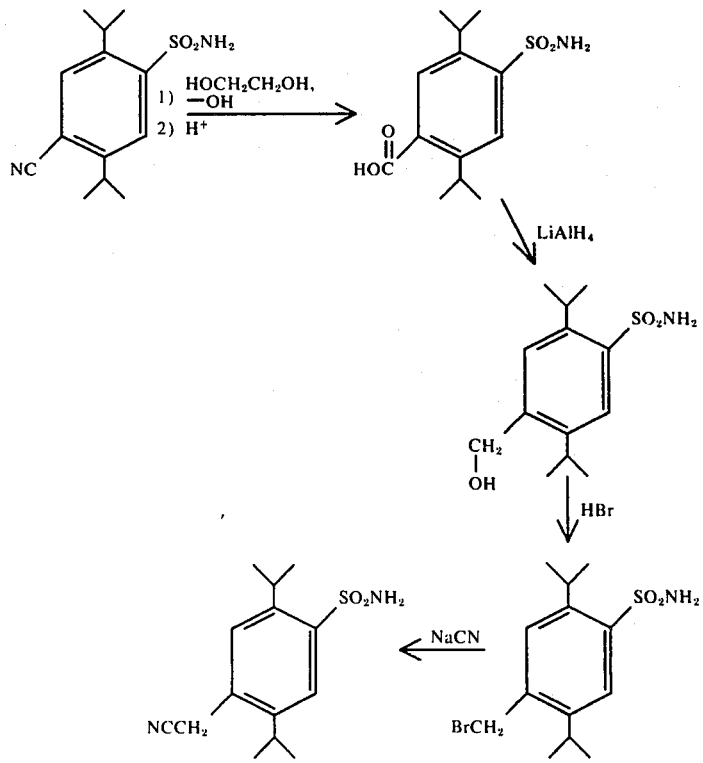

Nitrobenzenesulfonamides can be prepared as follows.

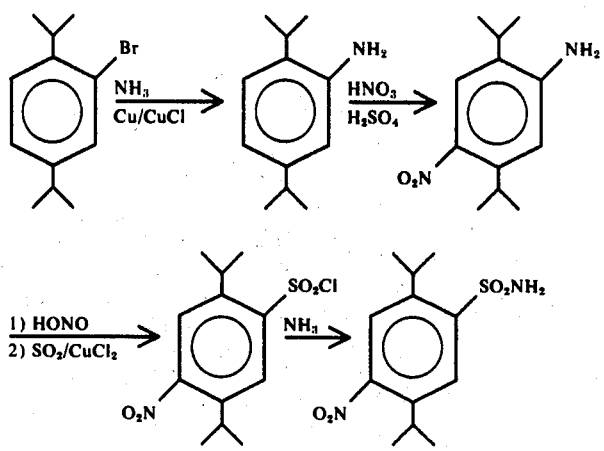

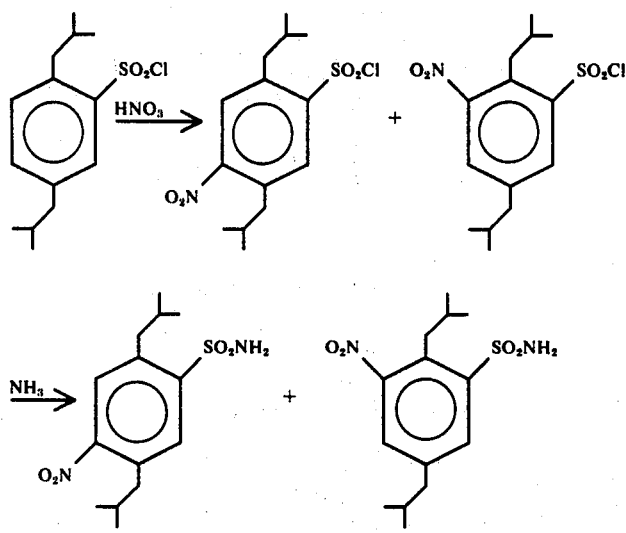

Alternatively:

Trifluoromethylbenzenesulfonamides can be prepared from cyanobenzenesulfonamides as follows.

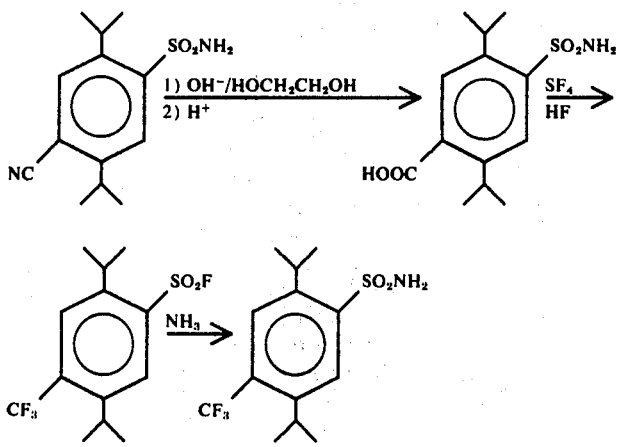

Compounds where Z is cyano are most active. When Z is halogen, chlorine and bromine are preferred. Compounds where Z is CN, Cl, or Br combine ease of manufacture and good activity.

Of the substituents $R_1$ to $R_4$ it is preferred for obtaining high activity that $R_1$ and $R_3$ are alkyl of 3–5 carbon atoms and $R_2$ and $R_4$ are hydrogen. It is most preferred that $R_1$ and $R_3$ are isopropyl.

It is preferred that $R_5$ is hydrogen and that $R_6$ is hydrogen, lithium, sodium or potassium.

Most preferred because of its safety to cotton and peanuts is 4-cyano-2,5-diisopropylbenzenesulfonamide and because of its safety to rice is 4-chloro-2,5-diisopropylbenzenesulfonamide.

The compounds of this invention are useful for general weed control or as selective herbicides. Preemergence surface applications are most useful but preplant incorporated or postemergence treatments are sometimes preferred. They provide control of many weeds with excellent selectivity in such crops as soybeans, wheat, rice, corn, sugarcane and cotton. General weed control on industrial sites and the like is provided by rates of 5 to 30 kg/ha. The compounds are most advantageously applied preemergence to crops at rates of 0.12 to 4 kg/ha, depending on the specific crop, the weed to be controlled, the soil and environmental conditions and the particular chemical used. Under certain conditions, such as lack of rainfall for an extended period after application, it is advantageous to lightly incorporate these compounds into the soil. Selected members of this class of compounds have postemergence activity and may be used at rates of 1 to 10 kg/ha for postemergence weed control, if applied while susceptible weeds are young, preferably in the two-leaf stage of development. Two or more compounds of this invention can be applied simultaneously.

Weeds controlled include, but are not limited to, crabgrass (*Digitaria* spp), barnyardgrass (*Echinochloa crusgalli*), junglerice (*Echinochloa colonum*), foxtail (*Setaria* spp.), witchgrass (*Panicum capillare*), goosegrass (*Eleusine indica*), pigweed (*Amaranthus* spp.), wild mustard (*Brassica* spp.), curly dock (*Rumex crispus*), Johnsongrass (*Sorghum halepense*) from seed, cheat (*Bromus secalinus*), downy brome (*Bromus tectorum*) and blackgrass (*Alopucurus mysuroides*).

It is sometimes advantageous to combine a compound of this invention with another herbicide in order to broaden the spectrum of weeds controlled or to increase the residual effect on industrial sites or to minimize the chances of injury to the current or subsequent crops. The exact combination which may be used to the best advantage will depend upon the weeds to be controlled, the environmental conditions or, in agricultural work, the crop being produced. The proper combination, however, can be readily selected by one with ordinary skill in the art. The use of these herbicides in combination with the herbicides of this invention will provide improved control of a wide variety of broad-leaved weeks including ragweed (*Ambrosia* spp.), lambsquarter (*Chenopodium album*), morningglory (*Ipomea* spp.), sicklepod (*Cassia obtusifolia*), smartweed (*Polygonum spp.*), flower-of-an-hour (*Hibiscus trionum*), cocklebur (*Xanthium spp.*), and velvetleaf (*Abutilon theoprasti*), as well as grasses of many types.

These compounds can be used in combination with other herbicides such as linuron (Lorox), atrazine (Aatrex), amiben (Amiben), 2,4-D (2,4-dichlorophenoxyacetic acid), molinate (Ordram), propanil (Stam or Rogue) and 3-(p-cumenyl)-1,1,-dimethylurea. Combinations of this type will broaden the spectrum of weeds controlled and reduce the rate of each herbicide used, thus reducing the chances of crop injury and persistence of the chemicals longer than necessary to provide weed control.

The preparation of representative halobenzenesulfonamides, cyanobenzenesulfonamides, nitrobenzenesulfonamides, trifluoromethylbenzenesulfonamides and cyanomethylbenzenesulfonamides is illustrated in the following examples, wherein all parts, proportions, and percentages are by weight and all temperatures are in degrees Centigrade unless indicated otherwise.

EXAMPLE 1

4-Bromo-2,5-diisopropylbenzenesulfonyl Chloride

To a one-liter flask containing 80 parts of 2-bromo-1,4-diisopropylbenzene in 320 parts of carbon tetrachloride, there is added over 15 min. 154 parts of chlorosulfonic acid. After stirring thirty min. longer, the reaction mixture is poured onto 1000 parts of ice. The organic layer is separated and washed with 200 parts of water and then dried over magnesium sulfate. Removal of the solvent under reduced pressure gives 105 parts of 4-bromo-2,5-diisopropylbenzenesulfonyl chloride which can be recrystallized from n-hexane, m.p. 80°–83°.

1,4-Diisopropyl-2-iodobenzene can be prepared by the method of H. Suzuki et al., Bull. Chem. Soc. (Japan) 39, 128 (1966); Org. Syn., 51, 94 (1971). 2-Fluoro-1,4-diisopropylbenzene can be prepared by halogen interchange with the iodo compound by heating with a large excess of potassium fluoride in refluxing DMF for 6 hr.

Similarly dialkyldihalobenzenesulfonyl chlorides can be prepared by appropriate substitution in the above example.

EXAMPLE 2

3-Chloro-2,5-diisopropylbenzenesulfonyl chloride

A sealed autoclave, charged with 288 parts of 2,5-diisopropylbenzenesulfonyl chloride, 5 parts of antimony pentachloride and 600 parts carbon tetrachloride and 36 parts chlorine, is shaken at 150° for 6 hr. The reaction solution is washed with sodium bisulfite and water. The washed solution is dried and the solvent distilled under reduced pressure. The crude residue can be recrystallized from a suitable solvent to give 3-chloro-2,5-diisopropylbenzenesulfonyl chloride.

Similarly dialkyldihalo- and dialkyltrihalobenzenesulfonyl chlorides can be prepared from dialkylhalo- and dialkyldihalobenzenesulfonyl chlorides by appropriate substitution in the above procedure. Where isomeric mixtures are obtained, the isomers can be separated by chromatography or fractional crystallization.

EXAMPLE 3

4-Bromo-2,5-diisopropylbenzenesulfonamide

To a one-liter flask containing 90 parts of concentrated aqueous ammonia and 150 parts of ether, there is added over three hours, 105 parts of 4-bromo-2,5-diisopropylbenzenesulfonyl chloride in 180 parts of ether. After stirring 2 hours longer, the excess ammonia is neutralized by adding 10% HCl. The organic layer is washed two times with 200 parts of saturated sodium chloride and is dried over sodium sulfate. Removal of the solvent gives 92 parts of 4-bromo-2,5-diisopropylbenzenesulfonamide which may be recrystallized from 1-chlorobutane, m.p. 145°–152°.

N-Alkyl- and N,N-dialkylbenzenesulfonamides can be prepared by replacement of ammonia with alkyl- or dialkylamines in the above example.

The following dialkylhalobenzenesulfonamides, dialkyldihalobenzenesulfonamides, and dialkyltrihalobenzenesulfonamides can be prepared from the listed dialkyl-benzenes, dialkylhalobenzenes and dialkyldihalobenzenes by the methods described in the above examples. Where isomeric mixtures are formed, the isomers are separated by chromatography or fractional crystallization.

TABLE 1

| Starting Material | Product |
| --- | --- |
| 4-tert-Butylethylbenzene | 5-tert-Butyl-3-chloro-2-ethylbenzenesulfonamide |
| 4-tert-Butylisopropylbenzene | 5-tert-Butyl-3-chloro-2-isopropylbenzenesulfonamide |
| 4-tert-Butylisobutylbenzene | 5-tert-Butyl-2-isobutyl-3-chloro-N,N-dimethyl-benzenesulfonamide |
| 4-tert-Butyl-sec-butylbenzene | 5-tert-Butyl-2-sec-butyl-3-chloro-N-methyl-benzenesulfonamide |
| 4-Isopropyl-n-propylbenzene | 3-Chloro-5-isopropyl-2-n-propyl-N-ethyl-benzenesulfonamide |
| 4-(1,1-Dimethylpropyl)isopropylbenzene | 3-Chloro-5-(1,1-dimethylpropyl)-2-isopropylbenzenesulfonamide |
| 1,4-Di-sec-butylbenzene | 3-Chloro-2,5-di-sec-butylbenzenesulfonamide |
| 4-sec-Butyl-n-propylbenzene | 5-sec-Butyl-3-chloro-2-n-propylbenzenesulfonamide |
| 2-bromo-1,4-diisopropylbenzene | N-allyl-4-bromo-2,5-diisopropylbenzenesulfonamide, m.p. 76–79° |
| 2-bromo-1,4-diisopropylbenzene | 4-Bromo-N-ethyl-2,5-diisopropylbenzenesulfonamide, m.p. 160–162° |
| 2-bromo-1,4-diisopropylbenzene | 4-Bromo-N-cyclopropyl-2,5-diisopropylbenzenesulfonamide, m.p. 138–140° |
| 4-(1,1,2,2-Tetramethylpropyl)ethylbenzene | 4-Chloro-5-ethyl-2-(1,1,2,2-tetramethylpropyl)-benzenesulfonamide |
| 2-Bromo-1,4-diisobutylbenzene | 4-Bromo-2,5-diisobutylbenzenesulfonamide, m.p. 108–112° |
| 2-Chloro-1,4-diisopropylbenzene | 4-Chloro-2,5-diisopropylbenzenesulfonamide, m.p. 141–146.5° |
| 2-Bromo-1,4-diisopropylbenzene | 4-Bromo-2,5-diisopropyl-N-methylbenzenesulfonamide, m.p. 186–189° |
| 2-Bromo-1,4-diisopropylbenzene | 4-Bromo-2,5-diisopropyl-N,N-dimethylbenzenesulfonamide, m.p. 111–114° |
| 2-Fluoro-1,4-diisopropylbenzene | 4-Fluoro-2,5-diisopropylbenzenesulfonamide |
| 4-Bromo-1,3-diisopropylbenzene | 5-Bromo-2,4-diisopropylbenzenesulfonamide |
| 2-Bromo-1,3-diisopropylbenzene | 3-Bromo-2,4-diisopropylbenzenesulfonamide |
| 3-Bromo-4-isobutylisopropylbenzene | 4-Bromo-5-isobutyl-2-isopropylbenzenesulfonamide m.p. 136–139° |
| 5-Bromo-1,3-diisopropylbenzene | 4-Bromo-2,6-diisopropylbenzenesulfonamide |
| 2,5-Dibromo-1,4-diisopropylbenzene | 2,5-Dibromo-3,6-diisopropylbenzenesulfonamide |
| 4,6-Dibromo-1,3-diisopropylbenzene | 3,5-Dibromo-2,6-diisopropylbenzenesulfonamide |
| 2,4-Dibromo-1,3-diisopropylbenzene | 3,5-Dibromo-2,4-diisopropylbenzenesulfonamide |
| 2-Bromo-1,4-di-n-propylbenzene | 4-Bromo-2,5-di-n-propylbenzenesulfonamide, m.p. 124–126.5° |
| 2,5-Dichloro-1,4-diisopropylbenzene | 3,6-Diisopropyl-2,4,5-trichlorobenzenesulfonamide |
| 2-Bromo-1,4-diethylbenzene | 4-Bromo-2,5-diethylbenzenesulfonamide, m.p. 175–178° |
| 2-Bromo-1,4-diethylbenzene | 4-Bromo-2,5-diethyl-N-methylbenzenesulfonamide, m.p. 78–82° |
| 2-Bromo-1,4-diethylbenzene | 4-Bromo-2,5-diethyl-N,N-dimethylbenzenesulfonamide, b.p. 131° (0.08 mm) |
| 2-Bromo-1,4-di-sec-butylbenzene | 4-Bromo-2,5-di-sec-butyl-N,N-dimethylbenzenesulfonamide |
| 2-Bromo-4-sec-butyl-isopropylbenzene | 4-Bromo-2-sec-butyl-5-isopropylbenzenesulfonamide b.p. 195° (0.3 mm) |
| 2-Bromo-sec-butyl-4-isopropylbenzene | 4-Bromo-5-sec-butyl-2-isopropyl-N-methylbenzenesulfonamide |
| 2-Bromo-1-ethyl-4-isopropylbenzene | 4-Bromo-5-ethyl-2-isopropyl-N-ethylbenzenesulfonamide |
| 2-Bromo-4-sec-butyl-n-propylbenzene | 4-Bromo-2-sec-butyl-5-n-propyl-N-allylbenzenesulfonamide |
| 2-Bromo-1-isobutyl-4-(1,2-dimethylpropyl)benzene | 4-Bromo-5-isobutyl-2-(1,2-dimethylpropyl)-N-n-propylbenzenesulfonamide |
| 2-Bromo-1-isopropyl-4-(1,1,2-trimethylpropyl)-benzene | 4-Bromo-5-isopropyl-2-(1,1,2-trimethylpropyl)-N,N-di-n-propylbenzenesulfonamide |
| 2-Bromo-4-sec-butyl-1-isopropylbenzene | 4-Bromo-2-sec-butyl-5-isopropyl-N-methylbenzenesulfonamide, m.p. 134–136° |
| 2-Bromo-4-sec-butyl-1-isopropylbenzene | 4-Bromo-2-sec-butyl-N,N-dimethyl-5-isopropyl-benzenesulfonamide, m.p. 78–83° |
| 4-Bromo-1-sec-butyl-3-isopropylbenzene | 5-Bromo-2-sec-butyl-4-isopropyl-N-propargyl-benzenesulfonamide |
| 4-Bromo-3-sec-butyl-1-isopropylbenzene | 5-Bromo-4-sec-butyl-2-isopropyl-N,N-diethyl-benzenesulfonamide |
| 4-Bromo-sec-butyl-3-isobutylbenzene | 5-Bromo-4-isobutyl-2-sec-butylbenzenesulfonamide |
| 4-Bromo-(1,2-dimethylpropyl)-3-ethylbenzene | 5-Bromo-2-(1,2-dimethylpropyl)-4-ethyl-N,N-dimethyl-benzenesulfonamide |
| 2-Bromo-n-propyl-4-(1,2,2-trimethylpropyl)-benzene | 5-Bromo-4-n-propyl-2-(1,2,2-trimethylpropyl)-N-methylbenzenesulfonamide |
| 2-Chloro-1,4-diisopropylbenzene | 4-Chloro-N,N-diallyl-2,5-diisopropylbenzenesulfonamide, b.p. 147–152° (0.13 mm) |
| 2-Chloro-1,4-diisopropylbenzene | 4-Chloro-N,N-diethyl-2,5-diisopropylbenzenesulfonamide, b.p. 126–131° (0.12 mm) |
| 2-Chloro-1,4-diisopropylbenzene | 4-Chloro-2,5-diisopropyl-N,N-dimethylbenzenesulfonamide, m.p. 101–104° |
| 2-Chloro-1,4-diisopropylbenzene | 4-Chloro-2,5-diisopropyl-N,N-dipropylbenzenesulfonamide |
| 1,4-Diisopropyl-2-iodobenzene | 2,5-Diisopropyl-4-iodobenzenesulfonamide, m.p. 160–164° |
| 2-Bromo-1,4-di-sec-butylbenzene | 4-Bromo-2,5-di-sec-butylbenzenesulfonamide, m.p. 116–124° |
| 2-Bromo-1,4-diisopropylbenzene | 4-Bromo-N,N-diallyl-2,5-diisopropylbenzene- |

TABLE 1-continued

| Starting Material | Product |
|---|---|
| | sulfonamide, b.p. 143° (0.05 mm) |

EXAMPLE 4

4-Cyano-2,5-diisopropylbenzenesulfonamide

A one-liter flask containing 92 parts of 4-bromo-2,5-diisopropylbenzenesulfonamide, 30 parts of cuprous cyanide, and 250 parts N-methylpyrrolidone is heated at 190°–200° for 2 hours. The reaction mixture is cooled to 100° and is then poured into 1000 parts water. The precipitated material is filtered. It is heated for 2 hours near reflux with 1000 parts water and 30 parts sodium cyanide. The reaction is cooled and the precipitate filtered to obtain 60 parts 4-cyano-2,5-diisopropylbenzenesulfonamide. The solid can be recrystallized from methanol, and then exhibits a m.p. of 200°–202°.

EXAMPLE 5

5-Bromo-2-cyano-3,6-diisopropylbenzenesulfonamide and 5-cyano-2-bromo-3,6-diisopropylbenzenesulfonamide A one-liter flask containing 38 parts 2,5-dibromo-3,6-diisopropylbenzenesulfonamide, 9 parts of cuprous cyanide, and 125 parts N-methylpyrrolidone is heated at 200° for 2 hrs. The reaction mixture is cooled to 100° and is then poured into 500 parts water. The precipitated material is filtered and then is heated for 2 hrs. near reflux with 500 parts water and 15 parts sodium cyanide. The reaction is cooled and the precipitate filtered to obtain a mixture of 5-bromo-2-cyano-3,6-diisopropylbenzenesulfonamide and 5-cyano-2-bromo-3,6-diisopropylbenzenesulfonamide. The mixture is separated by chromatography, and then the individual compounds are purified by recrystallization.

By appropriate substitution the following cranodialkylbenzenesulfonamides, cyanodialkylhalobenzenesulfonamides, and cyanodialkyldihalobenzenesulfonamides can be prepared.

TABLE 2

4-Cyano-2,5-di-n-propylbenzenesulfonamide, m.p. 104°–106.5°
4-Cyano-2,5-di-sec-butylbenzenesulfonamide, b.p. 190° (0.06 mm)
4-Cyano-2,5-di-sec-butyl-N,N-dimethylbenzenesulfonamide
2-sec-Butyl-4-cyano-5-isopropylbenzenesulfonamide, b.p. 198° (0.15 mm)
2-sec-Butyl-4-cyano-5-isopropyl-N-methylbenzenesulfonamide, m.p. 160°–163°
4-Cyano-5-ethyl-2-isopropyl-N-ethylbenzenesulfonamide
2-sec-Butyl-4-cyano-5-n-propyl-N-allylbenzenesulfonamide
4-Cyano-2,5-diisopropyl-N,N-dipropylbenzenesulfonamide
5-Isobutyl-4-cyano-2-(1,2-dimethylpropyl)-N-n-propylbenzenesulfonamide
4-Cyano-5-isopropyl-2-(1,1,2-trimethylpropyl)-N,N-di-n-propylbenzenesulfonamide
2-sec-Butyl-5-cyano-4-isopropyl-N-propargylbenzenesulfonamide
4-sec-Butyl-5-cyano-2-isopropyl-N,N-diethylbenzenesulfonamide
4-Isobutyl-2-sec-butyl-5-cyanobenzenesulfonamide
5-Cyano-2-(1,2-dimethylpropyl)-4-ethyl-N,N-dimethylbenzenesulfonamide
5-Cyano-4-n-propyl-2-(1,2,2,-trimethylpropyl-N-methylbenzenesulfonamide
5-tert-Butyl-3-cyano-2-ethylbenzenesulfonamide
5-tert-Butyl-3-cyano-2-isopropylbenzenesulfonamide
5-tert-Butyl-2-isobutyl-3-cyano-N,N-dimethylbenzenesulfonamide
4-Cyano-N,N-diallyl-2,5-diisopropylbenzenesulfonamide, b.p. 147° (0.07 mm)
4-Cyano-N,N-diethyl-2,5-diisopropylbenzensulfonamide, m.p. 91°–94°
4-Cyano-2,5-diisopropyl-N,N-dimethylbenzenesulfonamide, m.p. 138°–144°
4-Cyano-5-ethyl-2-(1,1,2,2-tetramethylpropyl)benzenesulfonamide
5-tert-Butyl-2-sec-butyl-3-cyanobenzensulfonamide
3-Cyano-5-isopropyl-2-n-propyl-N-ethylbenzenesulfonamide
3-Cyano-5-(1,1-dimethylpropyl)-2-isopropylbenzenesulfonamide
3-Cyano-2,5-di-sec-butylbenzenesulfonamide
3-Cyano-2-ethyl-5-(1,2,2-trimethylpropyl)benzenesulfonamide
4-Cyano-1,3-diisobutylbenzenesulfonamide
4-Cyano-1,3-diisopropyl-N-methylbenzenesulfonamide
4-Cyano-1,3-diisopropyl-N,N-dimethylbenzenesulfonamide
5-Cyano-2,4-diisopropylbenzenesulfonamide
3-Cyano-2,4-diisopropylbenzenesulfonamide
4-Cyano-5-isobutyl-2-isopropylbenzenesulfonamide, m.p. 111°–114°
4-Cyano-2,6-diisopropylbenzenesulfonamide
2-Bromo-5-cyano-3,6-diisopropylbenzenesulfonamide
2-Bromo-4-cyano-3,6-diisopropylbenzenesulfonamide
3-Bromo-5-cyano-2,6-diisopropylbenzenesulfonamide
3-Bromo-5-cyano-2,4-diisopropylbenzenesulfonamide
5-Bromo-3-cyano-2,4-diisopropylbenzenesulfonamide
3-Cyano-2,5-diisopropylbenzenesulfonamide
3-Cyano-2,6-diisopropylbenzenesulfonamide
4-Cyano-3,6-dibromo-2,5-diisopropylbenzenesulfonamide
3-Bromo-6-chloro-4-cyano-2,5-diisopropylbenzenesulfonamide
6-Bromo-3-chloro-4-cyano-2,5-diisopropylbenzenesulfonamide
3-Bromo-4-cyano-2,5-diisopropylbenzenesulfonamide
3-Chloro-4-cyano-2,5-diisopropylbenzenesulfonamide 2-sec-butyl-4-cyano-N,N-dimethyl-5-isopropylbenzenesulfonamide, b.p. 152° (0.35 mm)

4-Cyano-2,5-diethyl-N,N-dimethylbenzenesulfonamide, b.p. 142° (0.1 mm)

4-Cyano-2,5-diisopropyl-N-methylbenzenesulfonamide, m.p. 209–211°

4-Cyano-2,5-diisopropyl-N-ethylbenzenesulfonamide, m.p. 176°–179°

4-Cyano-2,5-diethylbenzenesulfonamide, m.p. 191–193°

4-Cyano-2,5-diethyl-N-methylbenzenesulfonamide, m.p. 86°–88°

N-allyl-4-cyano-2,5-diisopropylbenzenesulfonamide, b.p. 184° (0.15 mm)

EXAMPLE 6

2,6-Diisopropylbenzenesulfonyl Chloride

One equivalent part by weight of 2,6-diisopropylaniline is diazotized with 1.1 equivalent parts of sodium nitrite and 1.1 equivalent parts of hydrochloric acid in acetic acid at 0° to 5°. This solution is added dropwise with stirring to a solution of acetic acid containing 1 equivalent part of cuprous chloride and excess sulfur dioxide at 10°. When the addition is complete and nitrogen evolution ceases, the mixture is poured into ice water and the oily product extracted into ether. The organic layer is washed with water and dried over sodium sulfate. Removal of the solvent gives 2,6-diisopropylbenzenesulfonyl chloride which may be purified by distillation.

By appropriate substitution in the above procedure, the following benzenesulfonyl chloride are made.

TABLE 3

| Starting Material | Product |
| --- | --- |
| 4-Bromo-2,5-diisopropyl-3-nitroaniline | 4-Bromo-2,5-diisopropyl-3-nitrobenzenesulfonyl Chloride |
| 4-Bromo-2,5-diisobutyl-3-nitroaniline | 4-Bromo-2,5-diisobutyl-3-nitrobenzenesulfonyl Chloride |

Using the procedure of Example 6 for preparing sulfonyl chlorides from anilines followed by reaction of the sulfonyl chlorides with various amines or ammonia, the following 2,5-dialkyl-4-nitrobenzenesulfonamides are prepared:

TABLE 4

| Starting Material | Product |
| --- | --- |
| 2,5-Diisopropyl-4-nitroaniline | 2,5-Diisopropyl-4-nitrobenzenesulfonamide, mp. 190–194° (d) |
| 2,5-Diisopropyl-4-nitroaniline | 2,5-Diisopropyl-N,N-dimethyl-4-nitrobenzenesulfonamide, m.p. 148–151° |
| 2,5-Diisopropyl-4-nitroaniline | N,N-Diallyl-2,5-diisopropyl-4-nitrobenzenesulfonamide |
| 2-Isopropyl-5-(1,1,2-trimethylpropyl)-4-nitroaniline | 2-Isopropyl-5-(1,1,2-trimethylpropyl)-4-nitrobenzenesulfonamide |
| 2-Ethyl-5-isopropyl-4-nitroaniline | 2-Ethyl-5-isopropyl-4-nitrobenzenesulfonamide |

EXAMPLE 7

3,4-Dibromo-2,5-diisopropylbenzenesulfonamide

3-Amino-4-bromo-2,5-diisopropylbenzenesulfonamide is prepared by known general methods (L. F. Fieser and M. Fieser, Reinhold Publishing Corp., N. Y., 3rd ed., 1956, pgs 599–602) from 2,5-diisopropylaniline by acylation to 2,5-diisopropylacetanilide, bromination to 4-bromo-2,5-diisopropylacetanilide, hydrolysis to 4-bromo-2,5-diisopropylaniline, nitration to 4-bromo-2,5-diisopropyl-3-nitroaniline, diazotization in the presence of cuprous chloride and sulfur dioxide to 4-bromo-2,5-diisopropyl-3-nitrobenzenesulfonamide (method of Example 6) and reduction.

3-Amino-4-bromo-2,5-diisopropylbenzenesulfonamide is diazotized with 1.1 equivalent parts of sodium nitrite and 1.1 equivalent parts of hydrobromic acid at 5° in acetic acid. The diazonium mixture is added portionwise to a flask containing 2 equivalent parts of cuprous bromide and hydrobromic acid in 25 parts of water at reflux. When the nitrogen evolution ceases, the reaction mixture is cooled and the product which solidifies is filtered and washed with water. The product may be further purified by recrystallization from ethanol-water.

If hydrochloric acid is substituted for hydrobromic acid and cuprous cyanide for cuprous bromide, the 3-amino-4-bromo-2,5-diisopropylbenzenesulfonamide may be converted to 4-bromo-3-cyano-2,5-diisopropylbenzenesulfonamide.

By appropriate substitution in the above procedure, the following cyano and halobenzenesulfonamides are made.

TABLE 5

| Starting Material | Product |
| --- | --- |
| 3-Amino-4,6-dibromo-2,5-diisopropylbenzenesulfonamide | 3-Cyano-4,6-dibromo-2,5-diisopropylbenzenesulfonamide |
| 3-Amino-4,6-dibromo-2,5-diisobutylbenzenesulfonamide | 3-Cyano-4,6-dibromo-2,5-diisobutylbenzenesulfonamide |
| 3-Amino-4-bromo-2,5-diisopropylbenzensulfonamide | 4-Bromo-3-cyano-2,5-diisopropylbenzenesulfonamide |
| 3-Amino-4-bromo-2,5-diisobutylbenzenesulfonamide | 4-Bromo-3-cyano-2,5-diisobutylbenzenesulfonamide |
| 3-Amino-4,6-dibromo-2,5-diisopropylbenzenesulfonamide | 2,5-Diisopropyl-3,4,6-tribromobenzenesulfonamide |
| 3-Amino-4-bromo-6-chloro-2,5-diisopropylbenzenesulfonamide | 6-Chloro-3,4-dibromo-2,5-diisopropylbenzenesulfonamide |
| 3-Amino-4,6-dibromo-2,5-diisopropylbenzenesulfonamide | 3-Chloro-4,6-dibromo-2,5-diisopropylbenzenesulfonamide |
| 3-Amino-4,6-dibromo-2,5-diisobutylbenzenesulfonamide | 2,5-Diisobutyl-3,4,6-tribromobenzenesulfonamide |
| 3-Amino-4-bromo-6-chloro-2,5-diisobutylbenzenesulfonamide | 6-Chloro-3,4-dibromo-2,5-diisobutylbenzenesulfonamide |

TABLE 5-continued

| Starting Material | Product |
| --- | --- |
| 3-Amino-4,6-dibromo-2,5-diisobutylbenzenesulfonamide | 3-Chloro-4,6-dibromo-2,5-diisopropylbenzenesulfonamide |
| 3-Amino-4-bromo-2,5-diisopropylbenzenesulfonamide | 3,4-Dibromo-2,5-diisopropylbenzenesulfonamide |
| 3-Amino-4-bromo-2,5-diisopropylbenzenesulfonamide | 4-Bromo-3-chloro-2,5-diisopropylbenzenesulfonamide |
| 3-Amino-4-bromo-2,5-diisobutylbenzenesulfonamide | 3,4-Dibromo-2,5-diisobutylbenzenesulfonamide |
| 3-Amino-4-bromo-2,5-diisobutylbenzenesulfonamide | 4-Bromo-3-chloro-2,5-diisobutylbenzenesulfonamide |

EXAMPLE 8

Part A

4-Carboxy-2,5-diisopropylbenzenesulfonamide

Twenty parts 4-cyano-2,5-diisopropylbenzenesulfonamide is refluxed with 50 parts of potassium hydroxide and 400 parts of ethylene glycol under nitrogen for 24 hours. The cooled reaction mixture is diluted with 600 parts of water and acidified with hydrochloride acid. The precipitated product is filtered and washed with water. Drying gives 17 parts of 4-carboxy-2,5-diisopropylbenzenesulfonamide having a m.p. of 225°–231°.

PART B

4-Hydroxymethyl-2,5-diisopropylbenzenesulfonamide

4-Carboxy-2,5-diisopropylbenzenesulfonamide, 60 parts in 250 parts of ether and 350 parts of tetrahydrofuran is added dropwise to 24 parts of lithium aluminum hydride in 500 parts of ether at a rate where the ether refluxes gently. The reactants are then refluxed for 16 hours. Dilute hydrochloric acid is then added dropwise until the inorganic salts precipitate. The mixture is filtered and dried over sodium sulfate. After filtration and solvent removal there remains 41 parts of 4-hydroxymethyl-2,5-diisopropylbenzenesulfonamide having a m.p. of 185°–189°.

Part C

4-Bromomethyl-2,5-diisopropylbenzenesulfonamide

To 26 parts 4-hydroxymethyl-2,5-diisopropylbenzenesulfonamide dissolved in 100 parts chloroform heated just below reflux is added hydrogen bromide in a slow stream for an hour. The organic phase is washed with aqueous sodium bicarbonate, dried over magnesium sulfate and concentrated in vacuo to give 4-bromomethyl-2,5-diisopropylbenzenesulfonamide.

Part D

4-Cyanomethyl-2,5-diisopropylbenzenesulfonamide

To 32 parts 4-bromomethyl-2,5-diisopropylbenzenesulfonamide in 100 parts dimethylsulfoxide is added 10 parts sodium cyanide. The reaction is heated at 65°–70° for 30 minutes and then poured into ice water to give 4-cyanomethyl-2,5-diisopropylbenzenesulfonamide. Purification is accomplished by recrystallization or chromatography on Florisil, silica gel, alumina, etc., but the relatively pure reaction product is useful in the compositions and methods of this invention without purification.

The following cyanomethyldialkylbenzenesulfonamides, cyanomethylhalodialkylbenzenesulfonamides, and cyanomethyldialkyl-N,N-dialkyl (or N-alkyl) benzenesulfonamides are prepared from the corresponding cyanodialkylbenzenesulfonamides by appropriate substitution in the above sequence of procedures. Where isomeric mixtures are obtained, they can be separated by chromatography on Florisil, silica gel, alumina, etc., or by fractional crystallization, but the mixtures themselves are useful in the compositions and methods of this invention.

TABLE 6

4-Cyanomethyl-2,5-di-n-propylbenzenesulfonamide
2,5-Di-sec-butyl-4-cyanomethyl-N,N-dimethyl-benzenesulfonamide
2-sec-Butyl-4-cyanomethyl-5-isopropylbenzenesulfonamide
5-sec-Butyl-4-cyanomethyl-2-isopropyl-N-methylbenzenesulfonamide
4-Cyanomethyl-5-ethyl-2-isopropyl-N-ethylbenzenesulfonamide
2-sec-Butyl-4-cyanomethyl-5-n-propyl-N-allylbenzenesulfonamide
5-Isobutyl-4-cyanomethyl-2-(1,2-dimethylpropyl)-N-n-propylbenzenesulfonamide
4-Cyanomethyl-5-isopropyl-2-(1,1,2-trimethylpropyl)-N,N-di-n-propylbenzenesulfonamide
4-Cyanomethyl-5-n-propyl-2-(1,2,2-trimethylpropyl)-N,N-dimethylbenzenesulfonamide
2-sec-Butyl-5-cyanomethyl-4-isopropyl-N-propargylbenzenesulfonamide
4-sec-Butyl-5-cyanomethyl-2-isopropyl-N,N-diethylbenzenesulfonamide
4-Isobutyl-2-sec-butyl-5-cyanomethylbenzenesulfonamide
5-Cyanomethyl-2-(1,2-dimethylpropyl)-4-ethyl-N,N-dimethylbenzenesulfonamide
5-Cyanomethyl-4-n-propyl-2-(1,2,2-trimethylpropyl)-N-methylbenzenesulfonamide
5-tert-Butyl-3-cyanomethyl-2-ethylbenzenesulfonamide
5-tert-Butyl-3-cyanomethyl-2-isopropylbenzenesulfonamide
5-tert-Butyl-2-isobutyl-3-cyanomethyl-N,N-dimethylbenzenesulfonamide
5-tert-Butyl-2-sec-butyl-3-cyanomethylbenzenesulfonamide
3-Cyanomethyl-5-isopropyl-2-n-propyl-N-ethylbenzenesulfonamide
3-Cyanomethyl-5-(1,1-dimethylpropyl)-2-isopropylbenzenesulfonamide
3-Cyanomethyl-2,5-di-sec-butylbenzenesulfonamide
5-sec-Butyl-3-cyanomethyl-2-n-propylbenzenesulfonamide
3-Cyanomethyl-2-ethyl-5-(1,2,2-trimethylpropyl)-benzenesulfonamide
5-Cyanomethyl-1,4-diisobutylbenzenesulfonamide
5-Cyanomethyl-1,4-diisopropyl-N-methylbenzenesulfonamide 5-Cyanomethyl-1,4-diisopropyl-N,N-dimethylbenzenesulfonamide
5-Cyanomethyl-2,4-diisopropylbenzenesulfonamide
3-Cyanomethyl-2,4-diisopropylbenzenesulfonamide
4-Cyanomethyl-3-isobutyl-6-isopropylbenzenesulfonamide
4-Cyanomethyl-2,6-diisopropylbenzenesulfonamide
2-Bromo-5-cyanomethyl-3,6-diisopropylbenzenesulfonamide
2-Bromo-4-cyanomethyl-3,6-diisopropylbenzenesulfonamide
3-Bromo-5-cyanomethyl-2,6-diisopropylbenzenesulfonamide
3-Bromo-5-cyanomethyl-2,4-diisopropylbenzenesulfonamide
5-Bromo-3-cyanomethyl-2,4-diisopropylbenzenesulfonamide
3-Cyanomethyl-2,5-diisopropylbenzenesulfonamide
3-Cyanomethyl-2,6-diisopropylbenzenesulfonamide
3-Cyanomethyl-4,6-dibromo-2,5-diisopropylbenzenesulfonamide
3-Bromo-6-chloro-4-cyanomethyl-2,5-diisopropylbenzenesulfonamide
6-Bromo-3-chloro-4-cyanomethyl-2,5-diisopropylbenzenesulfonamide
3-Cyanomethyl-4,6-dibromo-2,5-diisobutylbenzenesulfonamide
3-Bromo-6-chloro-4-cyanomethyl-2,5-diisobutylbenzenesulfonamide
6-Bromo-3-chloro-4-cyanomethyl-2,5-diisobutylbenzenesulfonamide
4-Bromo-3-cyanomethyl-2,5-diisopropylbenzenesulfonamide
4-Bromo-3-cyanomethyl-2,5-diisobutylbenzenesulfonamide
3-Bromo-4-cyanomethyl-2,5-diisopropylbenzenesulfonamide
3-Chloro-4-cyanomethyl-2,5-diisopropylbenzenesulfonamide
3-Bromo-4-cyanomethyl-2,5-diisobutylbenzenesulfonamide
3-Chloro-4-cyanomethyl-2,5-diisobutylbenzenesulfonamide
4-Cyanomethyl-3,6-dibromo-2,5-diisopropylbenzenesulfonamide
4-Cyanomethyl-3,6-dibromo-2,5-diisobutylbenzenesulfonamide

EXAMPLE 9

5-tert-Butyl-2-ethyl-3-nitrobenzenesulfonyl Chloride 5-tert-Butyl-2-ethylbenzenesulfonyl chloride, 52 parts is added over ½ hour to 190 parts of fuming nitric acid and 25 parts of sulfuric acid at 0° to 10°. The reactants are stirred 2 hours at 0° to 10° and then at 25° for 2 hours. The reaction mixture is then poured onto ice. The product is extracted into methylene dichloride, which is washed with water and then dried over magnesium sulfate. Solvent removal gives 51 parts of the sulfonyl chloride which is pure enough to be used for the preparation of sulfonamides.

Using this procedure for preparing nitrobenzenesulfonyl chlorides, the corresponding nitrobenzene sulfonamides may be prepared using the procedures mentioned earlier for sulfonamide preparations from sulfonyl chlorides. In cases where a mixture of isomeric sulfonyl chlorides is obtained, the mixture is converted to a mixture of sulfonamdies which can be used as the mixture or chromatographed on alumina or selica gel to give the isomerically pure sulfonamides.

Table 7

| Starting Material | Product |
|---|---|
| 2,5-Diisobutylbenzenesulfonyl chloride | 2,5-Diisobutyl-3-nitrobenzenesulfonamide |
| 2,5-Dipropylbenzenesulfonyl chloride | 3-Nitro-2,5-dipropylbenzenesulfonamide |
| 2,5-Dipropylbenzenesulfonyl chloride | N,N-dialkyl-3-nitro-2,5-dipropylbenzenesulfonamide |

EXAMPLE 10

Part A 2,5-Diisopropyl-4-trifluoromethylbenzenesulfonyl Fluoride

4-Carboxy-2,5-diisopropylbenzenesulfonamide, 10 parts, sulfur tetrafluoride, 30 parts, and hydrogen fluoride, 12 parts is heated in a Hastelloy-lined bomb for 2 hours at 100°, 3 hours at 130°, and 5 hours at 145°. On cooling, the crude product is dissolved in methylene dichloride, treated with sodium fluoride and then filtered. Removal of the solvent gives 9.5 parts of 2,5-diisopropyl-4-trifluoromethylbenzenesulfonyl fluoride which may be purified by vacuum sublimation, and then exhibits a m.p. of 140°–146°.

Part B 2,5-Diisopropyl-4-trifluoromethylbenzenesulfonamide

A mixture of ammonia, 25 parts, and 2,5-diisopropyl-4-trifluoromethylbenzenesulfonyl fluoride, 7 parts, is heated for 4 hours at 100° in a Hastelloy-lined bomb. After removal of the ammonia, the crude product is stirred with water, dried. Pure product, m.p. 171°–174°, is obtained after vacuum sublimation.

Starting with cyanobenzenesulfonamides, the following trifluoromethylbenzenesulfonamides may be prepared following the above example. Various amines may be substituted for ammonia in Part B.

Table 8

| Starting Material | Product |
|---|---|
| 4-Cyano-2,5-diisopropylbenzenesulfonamide | 2,5-Diisopropyl-N-propyl-4-trifluoromethylbenzenesulfonamide |
| 4-Cyano-2,5-dipropylbenzenesulfonamide | 2,5-Dipropyl-4-trifluoromethylbenzenesulfonamide |
| 4-Cyano-2-ethyl-5-isopropylbenzenesulfonamide | 2-Ethyl-5-isopropyl-4-trifluoromethylbenzenesulfonamide |
| 4-Cyano-2,5-diisopropylbenzenesulfonamide | N,N-Diallyl-2,5-diisopropyl-4-trifluoromethylbenzenesulfonamide |
| 5-Cyano-2,4-diisopropylbenzenesulfonamide | 2,4-Diisopropyl-5-trifluoromethylbenzenesulfonamide |
| 3-Cyano-2,5-diisopropylbenzenesulfonamide | 2,5-Diisopropyl-3-trifluoromethylbenzenesulfonamide |
| 3-Bromo-4-cyano-2,5-diisopropylbenzenesulfonamide | 3-Bromo-2,5-diisopropyl-4-trifluoromethylbenzenesulfonamide |
| 3-Chloro-4-cyano-2,5-diisopropylbenzenesulfonamide | 3-Chloro-2,5-diisopropyl-4-trifluoromethylbenzenesulfonamide |

EXAMPLE 11

Methyl N-(4-Cyano-2,5-diisopropylphenylsulfonyl)formimidate

To a mechanically stirred mixture of 27 parts of 4-cyano-2,5-diisopropylbenzenesulfonamide and 22 parts trimethyl orthoformate was added a trace of p-toluenesulfonic acid. The reaction was heated at reflux for 4 hours. It was filtered, the filtrate stripped to dryness in vacuo, and the resulting solid recrystallized from methanol to give the title product, m.p. 130°–132°.

The following formimidic or acetimidic acid esters are prepared from the listed benzenesulfonamides and an ester selected from trimethyl or triethyl orthoformate or trimethyl or triethyl orthoacetate by the procedure of the above example.

TABLE 9

| Starting Material | Product |
| --- | --- |
| 4-cyano-2,5-diisopropylbenzenesulfonamide | ethyl N-(4-cyano-2,5-diisopropylphenylsulfonyl)-formimidate, m.p. 111–113° |
| 4-cyano-2,5-diisopropylbenzenesulfonamide | 4-cyano-N-(1-methoxyethylidene)-2,5-diisopropyl-benzenesulfonamide |
| 4-cyano-2,5-diisopropylbenzenesulfonamide | 4-cyano-N-(1-ethoxyethylidene)-2,5-diisopropyl-benzenesulfonamide, m.p. 102–105° |
| 4-chloro-2,5-diisopropylbenzenesulfonamide | methyl N-(4-chloro-2,5-diisopropylphenylsulfonyl)-formimidate, m.p. 81–83° |
| 4-chloro-2,5-diisopropylbenzenesulfonamide | ethyl N-(4-chloro-2,5-diisopropylphenylsulfonyl)-formimidate, m.p. 76–78° |
| 4-chloro-2,5-diisopropylbenzenesulfonamide | 4-chloro-N-(1-methoxyethylidene)-2,5-diisopropyl-benzenesulfonamide |
| 4-chloro-2,5-diisopropylbenzenesulfonamide | 4-chloro-N-(1-ethoxyethylidene)-2,5-diisopropyl-benzenesulfonamide |
| 4-bromo-2,5-diisopropylbenzenesulfonamide | methyl N-(4-bromo-2,5-diisopropylphenylsulfonyl)-formimidate |
| 4-bromo-2,5-diisopropylbenzenesulfonamide | ethyl N-(4-bromo-2,5-diisopropylphenylsulfonyl)-formimidate |
| 4-bromo-2,5-diisopropylbenzenesulfonamide | 4-bromo-N-(1-methoxyethylidene)-2,5-diisopropyl-benzenesulfonamide |
| 4-bromo-2,5-diisopropylbenzenesulfonamide | 4-bromo-N-(1-ethoxyethylidene)-2,5-diisopropyl-benzenesulfonamide |
| 4-cyano-5-isobutyl-2-isopropylbenzenesulfonamide | methyl N-(4-cyano-5-isobutyl-2-isopropylphenyl-sulfonyl)formimidate |
| 4-cyano-5-isobutyl-2-isopropylbenzenesulfonamide | 4-cyano-5-isobutyl-2-isopropyl-N-(1-methoxyethylidene)benzenesulfonamide |
| 4-chloro-5-isobutyl-2-isopropylbenzenesulfonamide | methyl N-(4-chloro-5-isobutyl-2-isopropylphenyl-sulfonyl)formimidate |
| 4-chloro-5-isobutyl-2-isopropylbenzenesulfonamide | 4-chloro-5-isobutyl-2-isopropyl-N-(1-methoxyethylidene)benzenesulfonamide |
| 4-chloro-5-isobutyl-2-isopropylbenzenesulfonamide | ethyl N-(4-chloro-5-isobutyl-2-isopropylphenyl-sulfonyl)formimidate |
| 2-sec-butyl-4-cyano-5-isopropylbenzenesulfonamide | methyl N-(2-sec-butyl-4-cyano-5-isopropylphenyl-sulfonyl)formimidate |
| 2-sec-butyl-4-cyano-5-isopropylbenzenesulfonamide | 2-sec-butyl-4-cyano-5-isopropyl-N-(1-methoxyethylidene)benzenesulfonamide |
| 2-sec-butyl-4-chloro-5-isopropylbenzenesulfonamide | methyl N-(2-sec-butyl-4-chloro-5-isopropylphenyl-sulfonyl)formimidate |
| 2-sec-butyl-4-chloro-5-isopropylbenzenesulfonamide | ethyl N-(2-sec-butyl-4-chloro-5-isopropylphenyl-sulfonyl)formimidate |
| 2-sec-butyl-4-chloro-5-isopropylbenzenesulfonamide | 2-sec-butyl-4-chloro-5-isopropyl-N-(1-methoxyethylidene)benzenesulfonamide |
| 4-chloro-2,5-di-sec-butylbenzenesulfonamide | methyl N-(4-chloro-2,5-di-sec-butylphenylsulfonyl)-formimidate |
| 4-cyano-2,5-di-sec-butylbenzenesulfonamide | methyl N-(4-cyano-2,5-di-sec-butylphenylsulfonyl)-formimidate |
| 5-chloro-2,4-diisopropylbenzenesulfonamide | methyl N-(5-chloro-2,4-diisopropylphenylsulfonyl)-formimidate |
| 5-cyano-2,4-diisopropylbenzenesulfonamide | methyl N-(5-cyano-2,4-diisopropylphenylsulfonyl)-formimidate |
| 4-cyanomethyl-2,5-diisopropylbenzenesulfonamide | methyl N-(4-cyanomethyl-2,5-diisopropylphenyl-sulfonyl)formimidate |
| 2,5-diisopropyl-4-nitrobenzenesulfonamide | methyl N-(2,5-diisopropyl-4-nitrophenylsulfonyl)-formimidate |
| 2,5-diisopropyl-4-trifluoromethylbenzenesulfonamide | methyl N-(2,5-diisopropyl-4-trifluoromethylphenyl-sulfonyl)formimidate |

EXAMPLE 12

N-Acetyl-4-cyano-2,5-diisopropylbenzenesulfonamide

A mechanically stirred mixture of 8 parts of 4-cyano-2,5-diisopropylbenzenesulfonamide and 50 parts of acetic anhydride was heated near reflux for 6 hours. The reaction was concentrated in vacuo to give a solid which was recrystallized from ethanol-water, and then exhibited a m.p. if 170°–173°.

The following N-acylsulfonamides are prepared from the listed benzenesulfonamides and the corresponding anhydrides by the procedure of the above example.

TABLE 10

| Starting Material | Product |
| --- | --- |
| 4-cyano-2,5-diisopropylbenzenesulfonamide | 4-cyano-2,5-diisopropyl-N-propionylbenzenesulfonamide |
| 4-chloro-2,5-diisopropylbenzenesulfonamide | N-acetyl-4-chloro-2,5-diisopropylbenzenesulfonamide |
| 4-chloro-2,5-diisopropylbenzenesulfonamide | 4-chloro-2,5-diisopropyl-N-formylbenzenesulfonamide |

TABLE 10-continued

| Starting Material | Product |
|---|---|
| 4-cyano-5-isobutyl-2-isopropylbenzenesulfonamide | N-acetyl-4-cyano-5-isobutyl-2-isopropylbenzenesulfonamide |
| 2-sec-butyl-4-cyano-5-isopropylbenzenesulfonamide | N-acetyl-2-sec-butyl-4-cyano-5-isopropylbenzenesulfonamide |
| 2-sec-butyl-4-chloro-5-isopropylbenzenesulfonamide | N-acetyl-2-sec-butyl-4-chloro-5-isopropylbenzenesulfonamide |
| 4-cyano-2,5-di-sec-butylbenzenesulfonamide | N-acetyl-4-cyano-2,5-di-sec-butylbenzenesulfonamide |
| 5-cyano-2,4-diisopropylbenzenesulfonamide | N-acetyl-5-cyano-2,4-diisopropylbenzenesulfonamide |
| 4-cyanomethyl-2,5-diisopropylbenzenesulfonamide | N-acetyl-4-cyanomethyl-2,5-diisopropylbenzenesulfonamide |
| 2,5-diisopropyl-4-nitrobenzenesulfonamide | N-acetyl-2,5-diisopropyl-4-nitrobenzenesulfonamide |
| 2,5-diisopropyl-4-trifluoromethylbenzenesulfonamide | N-acetyl-2,5-diisopropyl-4-trifluoromethylbenzenesulfonamide |

EXAMPLE 13

Potassium 4-Cyano-2,5-diisopropylbenzenesulfonamide

To a mechanically stirred mixture of 6 parts potassium hydroxide and 100 parts water was added 14 parts 4-cyano-2,5-diisopropylbenzenesulfonamide. The reaction was heated until most of the solid was in solution. The reaction was filtered, cooled, and concentrated to give the potassuim salt. It was dried with heat under vacuum, then exhibited a m.p. of 275°–280°.

The following salts are prepared from the listed benzenesulfonamides by treatment with the appropriate metallic hydroxide by the procedure of the above example.

TABLE 11

| Starting Material | Product |
|---|---|
| 4-cyano-2,5-diisopropylbenzenesulfonamide | sodium 4-cyano-2,5-diisopropylbenzenesulfonamide, m.p. 295–300° |
| 4-cyano-2,5-diisopropylbenzenesulfonamide | lithium 4-cyano-2,5-diisopropylbenzenesulfonamide |
| 4-cyano-2,5-diisopropylbenzenesulfonamide | calcium 4-cyano-2,5-diisopropylbenzenesulfonamide |
| 4-chloro-2,5-diisopropylbenzenesulfonamide | potassium 4-chloro-2,5-diisopropylbenzenesulfonamide, m.p. >300° |
| 4-chloro-2,5-diisopropylbenzenesulfonamide | sodium 4-chloro-2,5-diisopropylbenzenesulfonamide, m.p. >275° |
| 4-chloro-2,5-diisopropylbenzenesulfonamide | lithium 4-chloro-2,5-diisopropylbenzenesulfonamide |
| 4-chloro-2,5-diisopropylbenzenesulfonamide | calcium 4-chloro-2,5-diisopropylbenzenesulfonamide |
| 4-bromo-2,5-diisopropylbenzenesulfonamide | sodium 4-bromo-2,5-diisopropylbenzenesulfonamide, m.p. >250° |
| 4-bromo-2,5-diisopropylbenzenesulfonamide | potassium 4-bromo-2,5-diisopropylbenzenesulfonamide |
| 4-cyano-5-isobutyl-2-isopropylbenzenesulfonamide | sodium 4-cyano-5-isobutyl-2-isopropylbenzenesulfonamide |
| 4-cyano-5-isobutyl-2-isopropylbenzenesulfonamide | potassium 4-cyano-5-isobutyl-2-isopropylbenzenesulfonamide |
| 4-chloro-5-isobutyl-2-isopropylbenzenesulfonamide | sodium 4-chloro-5-isobutyl-2-isopropylbenzenesulfonamide |
| 4-chloro-5-isobutyl-2-isopropylbenzenesulfonamide | potassium 4-chloro-5-isobutyl-2-isopropylbenzenesulfonamide |
| 2-sec-butyl-4-cyano-5-isopropylbenzenesulfonamide | sodium 2-sec-butyl-4-cyano-5-isopropylbenzenesulfonamide |
| 2-sec-butyl-4-cyano-5-isopropylbenzenesulfonamide | potassium 2-sec-butyl-4-cyano-5-isopropylbenzenesulfonamide |
| 2-sec-butyl-4-chloro-5-isopropylbenzenesulfonamide | sodium 2-sec-butyl-4-chloro-5-isopropylbenzenesulfonamide |
| 2-sec-butyl-4-chloro-5-isopropylbenzenesulfonamide | potassium 2-sec-butyl-4-chloro-5-isopropylbenzenesulfonamide |
| -4-cyano-2,5-di-sec-butylbenzenesulfonamide | potassium 4-cyano-2,5-di-sec-butylbenzenesulfonamide |
| 4-chloro-2,5-di-sec-butylbenzenesulfonamide | sodium 4-chloro-2,5-di-sec-butylbenzenesulfonamide |
| 5-chloro-2,4-diisopropylbenzenesulfonamide | potassium 5-chloro-2,4-diisopropylbenzenesulfonamide |
| 5-cyano-2,4-diisopropylbenzenesulfonamide | sodium 5-cyano-2,4-diisopropylbenzenesulfonamide |
| 4-cyanomethyl-2,5-diisopropylbenzenesulfonamide | sodium 4-cyanomethyl-2,5-diisopropylbenzenesulfonamide |
| 2,5-diisopropyl-4-nitrobenzenesulfonamide | sodium 2,5-diisopropyl-4-nitrobenzenesulfonamide |
| 2,5-diisopropyl-4-nitrobenzenesulfonamide | potassium 2,5-diisopropyl-4-nitrobenzenesulfonamide |
| 2,5-diisopropyl-4-trifluoromethylbenzenesulfonamide | sodium 2,5-diisopropyl-4-trifluoromethylbenzenesulfonamide |

COMPOSITIONS

The compounds of Formula (1) can be formulated for herbicidal use in conventional ways. The formulations can be wettable or water-soluble powders, dusts, suspensions in water and/or organic solvents, solutions, emulsifiers, high-strength compositions, pellets or granules. Other herbicides can be tank-mixed with the compounds of Formula (1) in the form of finished formulations or they can be combined to give single formulations for reasons of convenience. The formulations will include inert carrier materials and/or surfactants which serve as wetting, emulsifying and/or dispersing agents. Anionic or nonionic surfactants are preferred; lists of suitable surfactants can be found in "Detergents and Emulsifiers Annual" (1971) by John W. McCutcheon, Inc. The formulations will contain about 2 to 99% by weight, of active compound or compounds, up to about 20% by weight of a surfactant, and/or up to about 98% by weight of inert solid or liquid carrier. For dusts or granules, 1 to 25% of active compound can be used, for pellets 5–50%, for solutions or suspensions 5–50%, for wettable powers 20–90%, for water-soluble powder 20–95%, and high-strength compositions 90–99%. In some instances the surfactant may be used at up to 5 times the amount of active which may improve the effectiveness of the active compound. This amount of surfactant is most conveniently applied as a tank-mix with the active components.

Organic liquids suitable for preparation of solutions, suspensions, and emulsifiable concentrates containing the compounds of Formula (1) include alcohols, glycols, mono- and dialkyl ethers of ethylene glycol and diethylene glycol, ketones, esters, sulfamides, amides, tetrahydrofuran, paraffinic hydrocarbons, aromatic hydrocarbons, and halogenated hydrocarbons. Choice of a liquid is dictated by the reactivity, the solubility of the active compound to be used and whether a suspension or solution is desired. Compounds of Formula (1) can be formulated as aqueous suspensions or solutions depending upon whether the sulfonamides or their salts are used.

Solid, inert carrier materials suitable for wettable powders, pellets and granules include natural clays, synthetic fine silicas, and other materials commonly used for this purpose.

Further information concerning the preparation of herbicidal formulations can be found in U.S. Pat. No. 3,235,357.

Some preferred herbicidal compositions and methods of this invention are illustrated by the following examples, wherein all parts, proportions, and percentages are by weight unless indicated otherwise.

EXAMPLE A

| | |
|---|---|
| 4-cyano-2,5-diisopropylbenzenesulfonamide | 51% |
| sodium N-methyl-N-oleoyltaurate | 3% |
| sodium lignin sulfonate | 2% |
| synthetic silica | 44% |

The above ingredients are blended, hammer-milled to pass a 0.25 mm screen, air-milled in a fluid-energy mill, and reblended.

The following compounds can be formulated in like manner. Ethyl-N-(4-cyano-2,5-diisopropylphenylsulfonyl)-formimidate, 3-chloro-2,5-diisopropyl-4-trifluoromethylbenzenesulfonamide and 2,5-diisobutyl-3-nitrobenzenesulfonamide.

One kilogram of the above formulation and one kilogram of 50% wettable linuron are suspended in 200 liters of water and applied preemergence to a hectare of soybeans planted in Butlertown slit loam soil. Compared with the results obtained on a control plot on which no herbicide is used, this treatment controls all weeds present without injury to the crop and it produces an excellent yield.

EXAMPLE B

| | |
|---|---|
| 4-chloro-2,5-diisopropylbenzenesulfonamide | 25% |
| diatomaceous earth | 63% |
| methylated cellulose | 1% |
| dioctyl sodium sulfosuccinate | 1% |
| synthetic silica | 10% |

The above ingredients are blended, hammer-milled to pass a 0.25 mm screen and reblended.

All compounds of this invention can be formulated in like manner.

Four kilograms of this formulation plus 1.25 kilograms of atrazine formulated as an 80% wettable powder are suspended in 250 liters of water and applied preemergence to a hectare of corn planted in Flanagan silt loam soil. The treatment give excellent control of a wide spectrum of both broadleaves and grasses without injury to the corn which produces a high yield.

EXAMPLE C

| | |
|---|---|
| 4-cyano-2,5-diisopropylbenzenesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting rather thick suspension may be applied directly, extended with oils, or emulsified in water.

Four kilograms of the above formulation are emulsified in 200 liters of water and applied preemergence to a hectare of soybeans planted in Norfolk sandy loam soil. The treatment controls a number of weeds, particularly weedly grasses, and the soybeans, grown without competition produce an excellent yield.

EXAMPLE D

| | |
|---|---|
| 4-cyano-2,5-diisopropyl-N,N-dimethyl-benzenesulfonamide | 4% |
| attapulgite granules (15–30 mesh, 0.59 - app. 1.25 mm) | 90% |
| dimethylformamide | 6% |

A 40% solution of the active ingredient in dimethylformamide is prepared by warming the two materials with stirring. This solution is then sprayed on the granules which are tumbled in a blender. The granules so prepared are suitable for application without removal of solvent.

Fifty kilograms of these granules are distributed preemergence over a hectare of cotton planted in silt loam soil. One kilogram of diuron 80% wettable powder is applied as a spray in water at the same time the granules are distributed. This treatment controls a wide variety of weeds without injury to the cotton, which grows and produces an excellent yield of high-quality lint.

EXAMPLE E

| | |
|---|---|
| 4-bromo-2,5-diisopropyl-N,N-dimethyl-benzenesulfonamide | 10% |
| 3-(3,4-dichlorophenyl)-1-methoxy-1-methylurea | 2.5% |
| calcium lignin sulfonate plus wood sugars | 15% |
| kaolinite clay | 61.5% |
| sodium sulfate | 10% |
| sodium lauryl sulfate | 1% |

The above ingredients are ground to pass a 0.3 mm screen, blended, moistened with water, extruded and cut into pellets. After drying, these pellets can be applied directly or they can be further subdivided into 30–60 mesh (0.25–0.59 mm) granules for more uniform application. All compounds of this invention can be formulated in like manner.

Twenty kilograms of the above granules are distributed behind the planter to a hectare of soybeans being planted in silt loam soil containing 3% organic matter. The treatment controls all weeks present, both broadleaves and grasses, without damage to the crop, which grows without weed competition and produces an excellent yield.

EXAMPLE F

| | |
|---|---|
| 4-cyano-2,5-diisopropylbenzene-sulfonamide | 98% |
| trimethylnonyl polyethylene glycol ether | 2% |

The above ingredients are blended, hammer-milled to pass a 0.25 mm screen and reblended. This composition can be used directly or as a source of active for other formulations.

One kilogram of the above formulation and one kilogram of fluometuron are tank-mixed in 400 liters of water and sprayed preemergence on a hectare of cotton planted in Commerce silt loam soil. The cotton emerges to a good stand and grows vigorously without competition from crabgrass, sprangletop (*Leptochloa* spp.) barnyard grass, pigweed, seedling Johnsongrass, goosegrass, ragweed, spotted spurge (*Euphorbia maculata* L.) or other weeds controlled by the treatment. To obtain similar results, tank mixes are made of the above formulation with one of several other herbicides including diuron at 0.8 kilogram, monuron at 1 kilogram, prometryne at 2 kilograms, norea at 2 kilograms and chloropropham at 4 kilograms per hectare.

EXAMPLE G

| | |
|---|---|
| 4-bromo-2,5-diisopropyl-N,N-dimethyl-benzenesulfonamide | 20% |
| octylphenyl polyethylene glycol ether | 2% |
| dimethylformamide | 78% |

The above ingredients are stirred together to produce a solution suitable for low-volume application.

Two liters per acre of the above formulation is diluted with dimethyl formamide to 10 liters and applied by airplane to recently planted, but not yet emerged, spring wheat to control downy bromegrass and other annual grasses which reduce wheat yields if allowed to compete with the wheat.

EXAMPLE H

| Aqueous Suspension | |
|---|---|
| 4-chloro-2,5-diisopropylbenzene-sulfonamide | 30% |
| hydrated attapulgite | 2% |
| calcium lignin sulfonate | 15% |
| sodium carbonate | 2% |
| sodium pentachlorophenate | 0.7% |
| water | 50.3% |

All the above ingredients except the water are blended and ground to pass a 20-mesh screen. The water is then added, and the mixture is sand-ground until the solid particles are smaller than 10 microns.

Three kilograms of the above formulation are mixed in 450 liters of water with mechanical agitation and sprayed preemergence on a hectare of soybeans planted in Gallion fine sandy loam. The soybeans emerge to a good stand and grow vigorously to maturity unencumbered by weeds such as barnyard grass, pigweed, foxtail, crabgrass and fall panicum (*Panicum dichotomiflorum*) which are controlled by the treatment.

EXAMPLE I

| | |
|---|---|
| 4-chloro-2,5-diisopropylbenzene sulfonamide | 6% |
| "Ordram" 63 (molinate)* | 4% |
| attapulgite granules (24–48 mesh) | 75% |
| dimethylformamide | 15% |

*S-ethyl hexahydro-1-H-azepine-1-carbothioate

The active ingredients are dissolved in the dimethylformamide with warming, and the solution is sprayed on the granules which are tumbled in a mixer. The granules are then screened to remove fines and packaged.

Ten kilograms of the above granules are spread uniformly on a hectare of rice paddy soon after the rice is transplanted. Numerous grass and broadleaf weeds are controlled without injury to the rice which provides exceptional yields due to growth unencumbered by competing weeds.

EXAMPLE J

| | |
|---|---|
| 4-cyano-2,5-diisopropylbenzene-sulfonamide | 60% |
| 3-(p-cumenyl)-1,1-dimethylurea | 15% |
| sodium alkylnaphthalenesulfonate | 2% |
| sodium N-methyl-N-oleoyltaurate | 3% |
| diatomaceous earth | 20% |

The above ingredients are blended and hammer-milled to particles nearly all below 50 microns and reblended.

Two kilograms of the above wettable powder are dispersed with mechanical agitation in 400 liters of water and sprayed preemergence on a hectare of cotton planted in Crowley silt loam soil. Many weeds are controlled while the cotton grows vigorously to maturity giving an excellent yield of lint.

EXAMPLE K

| | |
|---|---|
| 4-cyano-2,5-diisopropyl-N,N-dimethyl-benzenesulfonamide | 50% |
| 4-chloro-4-ethylamino-6-isopropyl-amino-s-triazine (atrazine) | 25% |
| attapulgite clay | 22% |
| sodium lignin sulfonate | 2% |
| dioctyl sodium sulfosuccinate | 1% |

The above ingredients are blended, hammer-milled to particles nearly all below 50 microns and reblended.

Four kilograms of the above formulation are dispersed in 450 liters of water and sprayed uniformly on a hectare of sugarcane before the weeds and the crop have emerged. The sprayed area remain free of weeds including crabgrass, goosegrass, seedling Johnsongrass, foxtail, pigweed and ragweed. The sugarcane grows vigorously and produce a high yield.

EXAMPLE L

| | |
|---|---|
| 4-bromo-2,5-diisopropyl-N,N-dimethyl-benzenesulfonamide | 30% |
| 3-(3,4-dichlorophenyl)-1,1-dimethyl-urea | 30% |
| sodium alkylnaphthalenesulfonate | 2% |
| sodium N-methyl-N-oleoyltaurate | 3% |
| finely divided synthetic silica | 2% |
| diatomaceous earth | 33% |

The above ingredients are blended, hammer-milled to pass a 50-mesh screen and reblended.

The formulation of this example is applied to a railroad right-of-way heavily infested with weeds. The use rate is 30 kilograms of formulation per hectare of area treated. The weeds on the test are quickly killed and reinfestation is prevented for a period of one year.

EXAMPLE M

| | |
|---|---|
| 4-cyano-2,5-diisopropylbenzene-sulfonamide | 25% |
| 5-bromo-3-sec-butyl-6-methyluracil (bromacil) | 25% |
| sodium N-methyl-N-oleoyltaurate | 3% |
| sodium alkylnaphthalenesulfonate | 2% |
| diatomaceous earth | 45% |

The above ingredients are blended, hammer-filled to particles nearly all below 50 microns and reblended.

The following compounds can take the place of the 4-cyano-2,5-diisopropylbenzenesulfonamide: methyl N-(4-cyano-2,5-diisopropylphenylsulfonyl)formimidate N-acetyl-4cyano-2,5-diisopropylbenzenesulfonamide 2,5-diisopropyl-4-trifluoromethylbenzenesulfonamide 3-nitro-2,5-dipropylbenzenesulfonamide.

Forty kilograms of the above formulation are applied to a hectare of land in a tank farm area. An existing population of weeds is quickly killed and the area kept free of plant growth for a period of many months.

EXAMPLE N

| | |
|---|---|
| 4-chloro-2,5-diisopropylbenzene-sulfonamide | 15% |
| 3-(p-cumenyl)-1,1-dimethylurea | 15% |
| paraffinic hydrocarbon oil | 61% |
| polyoxyethylene sorbitol heptaoleate | 8% |
| synthetic fine silica | 1% |

The ingredients are combined and sand-milled to produce particles essentially all below 5 microns. For application, the product can be extended with either oils or water. An emulsion is formed in the latter.

Four liters of the above formulation are added to a 2000 liter spray tank filled with water and provided with continuous bypass agitation. The emulsion is sprayed on a hectare of direct seeded rice. The treatment controls barnyardgrass, junglerice and many other weeds in the field. The rice grows well without weed competition and produces a good yield.

EXAMPLE O

| | |
|---|---|
| sodium 4-cyano-2,5-diisopropylbenzenesulfonamide | 95.0% |
| sodium lauryl sulfate | 0.5% |
| finely divided synthetic silica | 4.5% |

The above ingredients are blended, ground to pass an 0.42 mm screen and reblended to form a water-soluble powder. The following compounds can be formulated in like manner:

potassium 4-cyano-2,5-diisopropylbenzenesulfonamide
   sodium 4-chloro-2,5-diisopropylbenzenesulfonamide
   potassium 4-chloro-2,5-diisopropylbenzenesulfonamide One kilogram of the above formulation is dissolved in 400 liters of water and sprayed preemergence to an acre of cotton planted on a Boskett silt loam soil with 2% organic matter. Weeds infesting the area consisting primarily of crabgrass, brachiaria, sprangletop, barnyardgrass, pigweed and ragweed, are controlled. The cotton grows vigorously to maturity.

EXAMPLE P

| | |
|---|---|
| lithium 4-cyano-2,5-diisopropylbenzenesulfonamide | 24.0% |
| ethylene glycol | 50.0% |
| methanol | 4.0% |
| ethanol | 5.0% |
| water | 17.0% |

The above ingredients are blended with warming to produce a water-soluble liquid concentrate.

The above formulation is dissolved in water at the rate of one liter per 100 liters of solution. The dilute solution is sprayed preemergence at a volume rate of 400 liters per hectare on a Cecil sandy loam soil with 1.9% organic matter planted to soybeans. The soybeans grow to maturity producing a high yield without competition from weeds which were eliminated by the above treatment.

EXAMPLE Q

| | |
|---|---|
| 4-chloro-2,5-diisopropylbenzenesulfonamide | 22.0% |
| lithium hydroxide monohydrate | 4.0% |
| ethylene glycol | 35.0% |
| methanol | 4.0% |
| water | 35.0% |

The above ingredients are blended with warming to produce a water-soluble liquid concentrate.

One part of the above liquid concentrate is dissolved in 9 parts of water and sprayed preemergence by airplane at a volume rate of 30 liters per hectare on rice drill planted in a Crowley silt loam soil. Barnyardgrass, sprangletop and dayflower are controlled, allowing the rice to row unencumbered by serious weed competition, thereby producing a good yield of grain.

EXAMPLE R

| | |
|---|---|
| methyl N-(4-cyano-2,5-diisopropylphenylsulfonyl)-formimidate | 20.0% |
| xylene | 25.0% |
| isophorone | 51.0% |
| blend of oil-soluble sulfonates and polyethoxyethylene ethers | 4.0% |

The above ingredients are blended with warming to form an emulsifiable concentrate. The following compounds can be formulated in like manner:

ethyl N-(4-cyano-2,5-diisopropylphenylsulfonyl)formimidate 4-cyano-N-(1-ethoxyethylidene)-2,5diisopropylbenzenesulfonamide methyl N-(4-chloro-2,5-diisopropylphenylsulfonyl)formimidate ethyl N-(4-chloro-2,5-diisopropylphenylsulfonyl)formimidate This formulation is emulsified with water in a volume ratio of 1 to 7 and sprayed preemergence by airplane at the rate of 20 liters of spray per hectare on Riverdale clay loam recently planted to spring wheat. Wild oats and cheatgrass are controlled and the wheat matures to produce a good yield.

In the following composition claims, the term "consisting essentially of" means that in addition to the recited components the composition also may contain other components which do not adversely affect its effectiveness for the intended use.

I claim:
1. A compound of the formula

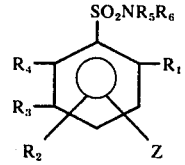

where
Z is chlorine or bromine;
$R_2$, $R_4$ and $R_5$ are hydrogen;
$R_6$ is hydrogen, lithium, potassium, or sodium;
$R_1$ is alkyl of 3 to 5 carbon atoms; and
$R_3$ is alkyl of 3 to 5 carbon atoms.
2. The compound of claim 1: 4-chloro-2,5-diisopropylbenzenesulfonamide.

* * * * *